(12) United States Patent
Blankenstein et al.

(10) Patent No.: US 7,713,906 B2
(45) Date of Patent: May 11, 2010

(54) CATALYST COMPOSITION, PROCESS FOR ITS PREPARATION AND USE THEREOF

(75) Inventors: Paul Blankenstein, Amsterdam (NL); Mark Crocker, Amsterdam (NL); Carl Johan Gerrit Van Der Grift, Rodange (LU); Johannes Jacobus Maria Van Vlaanderen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1333 days.

(21) Appl. No.: 10/312,099

(22) PCT Filed: Jun. 21, 2001

(86) PCT No.: PCT/EP01/07080

§ 371 (c)(1), (2), (4) Date: Mar. 10, 2003

(87) PCT Pub. No.: WO01/97967

PCT Pub. Date: Dec. 27, 2001

(65) Prior Publication Data

US 2003/0166951 A1  Sep. 4, 2003

(51) Int. Cl.
  *B01J 21/00*  (2006.01)
  *C07D 301/14*  (2006.01)
  *C07D 301/12*  (2006.01)
  *C07D 301/06*  (2006.01)

(52) U.S. Cl. .......... 502/242; 502/236; 502/239; 549/525; 549/529; 549/531; 549/532

(58) Field of Classification Search .......... 502/242, 502/236, 239; 549/529, 525, 531, 532
See application file for complete search history.

(56) References Cited

U.S. PATENT DOCUMENTS

| | | | |
|---|---|---|---|
| 3,829,392 A | 8/1974 | Wulff | |
| 3,923,843 A | 12/1975 | Wulff | |
| 4,367,342 A | 1/1983 | Wulff et al. | |
| 4,410,501 A | 10/1983 | Taramasso et al. | |
| 4,888,319 A * | 12/1989 | Daamen et al. | 502/235 |
| 5,041,652 A * | 8/1991 | Padovan et al. | 564/267 |
| 5,808,136 A | 9/1998 | Tacke et al. | |
| 6,008,389 A * | 12/1999 | Grosch et al. | 549/533 |
| 6,011,162 A | 1/2000 | Han et al. | |
| 6,114,552 A * | 9/2000 | Han et al. | 549/529 |
| 6,255,499 B1 * | 7/2001 | Kuperman et al. | 549/523 |
| 2005/0014960 A1 | 1/2005 | Buijink et al. | 549/533 |

FOREIGN PATENT DOCUMENTS

| | | |
|---|---|---|
| DE | 3803895 C1 | 4/1989 |
| DE | 3912504 A1 | 10/1990 |
| EP | 0 309 048 A1 | 3/1989 |
| EP | 0 323 663 A2 | 7/1989 |
| EP | 0 345 856 A1 | 12/1989 |
| EP | 0 734 764 A3 | 10/1996 |
| GB | 1249079 | 10/1971 |
| GB | 1 332 527 | 10/1973 |
| JP | 11-228553 | 8/1999 |
| NL | 145233 | 3/1975 |
| NL | 1008686 | 3/1998 |
| WO | 98/50374 A2 | 11/1998 |
| WO | 98/50374 A3 | 11/1998 |

* cited by examiner

*Primary Examiner*—Janet L. Andres
*Assistant Examiner*—Raymond Covington

(57) ABSTRACT

A catalyst composition comprising titanium incorporated into a silica support, characterized in that the silica support is a shaped extrudate of silica powder. The catalyst composition is useful in the epoxidation of olefins into alkylene oxides using organic hydroperoxides. The composition can be prepared by extruding silica powder into an extrudate having a selected shape; calcining the extrudate; impregnating the extrudate with a titanium-containing impregnating agent; and drying and calcining the impregnated extrudate.

16 Claims, No Drawings

CATALYST COMPOSITION, PROCESS FOR ITS PREPARATION AND USE THEREOF

FIELD OF THE INVENTION

The present inventions concerns an epoxidation catalyst composition for the epoxidation of olefins into alkylene oxides. The invention also concerns a process for the preparation of such catalyst composition and the use of the catalyst composition.

BACKGROUND OF THE INVENTION

Catalyst compositions based on the titanium-containing compounds supported on inorganic siliceous solid carriers for use in the epoxidation of olefins into alkylene oxides are well known in the art. Examples of such catalysts are, for instance, described in U.S. Pat. No. 4,367,342 and EP-A-345856. U.S. Pat. No. 4,367,342 discloses the use of inorganic oxygen compounds of silicon in chemical composition with at least 0.1% by weight of an oxide or hydroxide of titanium, while EP-A-345856 discloses a titania-on-silica heterogeneous catalyst which is obtainable by impregnating a silicon compound with a stream of gaseous titanium tetrachloride followed by calcinations and hydrolysis steps and optionally a silylation step.

More recently, titania-on-siliceous support type catalysts have also been described in U.S. Pat. No. 6,011,162; EP-A-734764 and Nf-A-1008686. These references also list suitable siliceous support materials including silica-containing refractory oxides such as silica-alumina and silica-magnesia, highly crystalline materials such as high silica-zeolites, silica-containing molecular sieves and amorphous silica. All these support materials have in common that they have a porous structure.

For instance, EP-A-734764 mentions silicates and silica, the latter preferably being synthetic porous silica composed of amorphous silica particles coagulated or bound to one another. Specific examples mentioned are silica gel, precipitated silica, silica powders like fumed pyrogenic silicas and several crystalline alumino-silicates. In NL-A-1008686 synthetic porous silica composed of amorphous silica particles coagulated or bound to one another is mentioned. Specific examples described are silica gel, precipitated silica, fumed pyrogenic silicas and crystalline porous silicas such as high silica content zeolites as exemplified by silicalite. Also the non-crystalline molecular sieve material MCM-41 is mentioned as a suitable material. In U.S. Pat. No. 6,011,162 synthetic porous silicas consisting of particles of amorphous silica flocculated or linked together so that they form relatively dense, close-packed masses, are described as suitable inorganic siliceous materials. Specific examples mentioned are silica gel and precipitated silica. Also mentioned are synthetic silica powders consisting of particles of amorphous silica flocculated in open-packed aggregates, which are exemplified by fumed pyrogenic silicas. Another class of suitable materials mentioned in U.S. Pat. No. 6,011,162 is the class of refractory oxides such silica-alumina, silica-magnesia, silica-zirconia and the like. Furthermore, siliceous molecular sieves like MCM-41, MCM-48 and M41S are mentioned.

However, all three references discussed in the previous paragraph eventually appoint silica gel as the preferred support material. This is, for instance, illustrated by the fact that in all working examples given in these references a silica gel is used as the carrier material.

In general, silica gels contain three-dimensional networks of aggregated silica particles of colloidal dimensions and are typically prepared by acidifying an aqueous sodium silicate solution to a pH of less than 11 by combining it with a strong mineral acid. The acidification causes the formation of monosilicilic acid ($Si(OH)_4$), which polymerizes into particles with internal siloxane linkages and external silanol groups. At a certain pH the polymer particles aggregate, thereby forming chains and ultimately gel networks. Silicate concentration, temperature, pH and the addition of coagulants affect gelling time and final gel characteristics such as density, strength, hardness, surface area and pore volume. The resulting hydrogel is washed free of electrolytes, dried and activated. The drying procedure affects the gel characteristics. Once the dried silica gel particles are obtained their shape is fixed and their dimensions can only be reduced by temperature treatment.

Although the silica gel particles are an excellent material to be used as support material for titania-on-silica catalysts, there is still room for improvement. First of all, silica gel particles cannot be shaped into any desired form. Generally, silical gel particles are spherical, e.g. obtained by spray-drying the gel or by spraying the gel into an immiscible liquid (emulsion polymerization). Alternatively, granular gel particles are used or, if being too large, are crushed into smaller granules. If such gel particles are packed into a bed, they consequently do not have an optimum shape to minimise the pressure drop across the catalyst bed when the bed is in operation. Especially with small gel particles the pressure drop poses a problem. On the other hand, small catalyst particles are favourable as in that way the effective diffusion length can be decreased and thus more active sites can participate in the reaction, thereby resulting in reduced residence times of the feed. Such shorter residence time is favourable as it means less secondary reactions and hence an improved selectivity. In practice, therefore, a balance is sought in terms of gel particle size between a high number of active sites and an acceptable pressure drop across the catalyst bed.

A further problem with gel particles is their mechanical strength. Although the strength of these particles is acceptable, it is generally insufficient to allow re-use of spent catalyst particles. Therefore, an increased mechanical strength would be desirable.

As indicated herein before the pore structure and surface characteristics of the gel particles are determined in the gelling and drying stage. Consequently, the characteristics of a dried gel particle, i.e. the form in which these particles are normally commercially available, can no longer be modified. U.S. Pat. No. 5,808,136 describes a catalyst for making vinyl acetate monomer, which catalyst contains palladium, gold and alkali acetate as catalytically active components on a support of silicon dioxide, alumosilicate or aluminium oxide. Silica is used in the form of tablets (see Comparative Example 2 and DE-C-3803895 and DE-A-3912504). Moulding silica powder into tablets is a discontinuous, relatively complicated preparation route.

U.S. Pat. No. 6,008,389 discloses oxidation catalysts based on titanium silicate extrudates having a zeolite structure, to which support subsequently is applied from 0.01 to 30% by weight of one or more noble metals selected from the group consisting of ruthenium, rhodium, palladium, osmium, iridium, platinum, rhenium, gold and silver. Contrary to the catalyst of the present invention, these catalysts are not obtained from a silica support to which subsequently titanium is chemically bonded.

SUMMARY OF THE INVENTION

It has now been found that the aforementioned shortcomings of using silica gel particles as catalyst support material can be overcome by using a silica extrudate as support material. Namely, an extrudate can be made in any desired shape, so that it is possible to use catalyst particles having a shape which optimally reduces the pressure drop while at the same time maximizing the number of active sites available. Furthermore, extrudates generally have a higher mechanical strength than gel particles. Finally, the pore structure and surface characteristics of silica extrudates can be effectively steered by the extrusion procedure and auxiliaries used therein. Consequently, it is possible to modify the intrinsic properties of the commercially available silica powder, which is used as the starting material for making the extrudates.

Accordingly, in a first aspect the present invention relates to an epoxidation catalyst composition comprising titanium chemically bonded to a silica support comprising a shaped extrudate of silica powder by impregnating the extrudate of silica powder with a titanium-containing impregnating agent.

DETAILED DESCRIPTION OF THE INVENTION

The silica powder used can originate from different silica sources. It could, for instance, be derived from fumed silica or silicalite. Suitably, however, the silica powder is a precipitated silica powder or a silica gel grinded into a powder. Such grinding can be performed by any suitable grinding means known in the art. In general, the silica powder particles will have an average particle size of 1 to 100 μm, although larger particles could also be used. The silica powder preferably contains at least 99 wt % of silica. More preferably, the silica powder consists of silica.

Precipitated silica powder is composed of aggregates of silica particles of colloidal size that have not become linked in a massive gel network during the preparation, but instead have coagulated into distinct solid particles. Precipitated silica is typically prepared by precipitation from a solution with a high sodium silicate concentration under certain specific pH conditions and using certain specific coagulants. Alternatively, precipitated silica can be prepared by adding aqueous ammonium hydroxide to ethyl silicate in alcohol. In general, ultimate and aggregate particle size in precipitated silica prepared from an aqueous sodium silicate solution can be varied by reinforcement and control of suspension pH, temperature and salt content. These procedures are known in the art. Suitable precipitated silica powders consist for at least 90 wt %, preferably for at least 95 wt % and more preferably for 98 wt % or more of silicium dioxide. The powders preferably have a specific surface area (BET) of from 200 to 800 m$^2$/g and an average particle size of 1 to 100 μm. Such powders are commercially available from several suppliers like Degussa and Crossfield.

The titanium present in the catalyst composition of the invention suitably is present in the form of titanium oxide or titanium hydroxide, more suitably titanium oxide. It is believed that the titanium is bonded via one, two or three oxygen atoms to respectively one, two or three silicon atoms which form part of the silica network. This is, for instance, described in EP-A-345856.

The amount of titanium (as metallic titanium) will normally be in the range of from 0.1 to 10% by weight, suitably 1 to 5% by weight, based on total weight of the catalyst. Preferably, titanium or a titanium compound, such as a salt or an oxide, is the only metal and/or metal compound present.

The catalyst composition is suitably obtained by impregnating the extrudates of silica powder with a titanium-containing impregnating agent. It was found particularly advantageous to calcine these extrudates at a temperature in the range of from 400 to 1000° C., preferably 450 to 800° C. and more preferably 500 to 700° C., prior to the impregnation. Further details of the preparation process of the catalyst composition of the present invention will be discussed herein after.

The final extrudates of silica powder, i.e. the extrudates which are actually being impregnated, suitably have a surface area (as determined by BET method ISO 9277: 1995(E)) in the range of from 100 to 1000 m$^2$/g, preferably from 150 to 700 m$^2$/g and more preferably 200 to 500 m$^2$/g, a pore volume (as determined by mercury intrusion) in the range of from 0.5 to 2.5 ml/g, preferably 0.7 to 2.0 ml/g and more preferably 0.8 to 1.5 ml/g, and a pore diameter as determined by mercury intrusion in the range of from 3 to 40 nm, preferably 4 to 30 nm and more preferably 4 to 20 nm.

One of the advantages of using extrudates is that their shape can easily be varied. For instance, the shape of the extrudate of precipitated silica powder can suitably be selected from a sphere, a trilobe, a quadrulobe, a ring, a massive cylinder and a hollow cylinder and the average particle size of the extrudate ranges from 0.5 to 10 mm. When using a spherically shaped extrudate, the wet extrudate is first spheronised in a suitable spheronising device before calcination. The way in which the particle size is defined varies with the actual shape of the particle, but the size given refers to the size definitions normally used. For instance, for spheres the average particle size refers to the diameter of the sphere, for rings to the outer diameter of the ring. For cylinders, it refers to the diameter of the circular cross-section of the cylinder and for tri- and quadrulobes to the distance between the tangents of two opposite lobes. In case of particle shapes having a length-component, the length/diameter ratio will normally be in the range of 1 to 5.

However, shapes other than those mentioned and sizes outside the range indicated may also be used.

In a second aspect the present invention relates to a process for the preparation of a heterogeneous catalyst suitable for the epoxidation of olefins into alkylene oxides, which process comprises the steps of:
(a) extruding silica powder into an extrudate having a selected shape;
(b) calcining the extrudate;
(c) impregnating the extrudate with a titanium-containing impregnating agent; and
(d) drying and calcining the impregnated extrudate.

In step (a) the silica powder is extruded into an extrudate. This can be performed by conventional extrusion methods and techniques known in the art, such as e.g. disclosed in EP-A-309048. Typically an extrusion mixture is prepared from the solids (silica powder and optionally binder), water and extrusion aids by mixing and kneading the ingredients into a shapable dough and passing this dough into the extruder.

In addition to the silica powder a binder material may be used. Suitable binder materials include inorganic oxides like silica, magnesia, titania, alumina, zirconia and silica-alumina, of which silica is preferred. The weight ratio of binder to silica powder material may vary from 0:100 to 90:10. For the purpose of the present invention the silica powder is suitably extruded without additional binder material. However, if used, it is preferred to use the binder material in a weight ratio of binder to silica powder material of from 10:90 to 50:50.

Beside the silica powder, optional binder and water the extrusion paste will normally also comprise extrusion aids to improve the flow properties. Extrusion aids are known in the art and may include flocculation agents, which normally are polyelectrolytes. Further extrusion aids include, for instance, ammonia and ammonia-releasing compounds like ammonium hydroxide, aliphatic mono-carboxylic acids, polyvinyl pyridine, and sulfoxonium, sulfonium, phosphonium and iodonium compounds, alkylated aromatic compounds, acyclic monocarboxylic acids, fatty acids, sulfonated aromatic compounds, alcohol sulfates, ether alcohol sulfates, sulfated fats and oils, phosphonic acid salts, polyoxyethylene alkylphenols, polyoxyethylene alcohols, alkanolamines (e.g. monoethanolamine), polyoxyethylene alkylamines, polyoxyethylene alkylamides, polyacrylamides, polyacryl amines, polyols, polyvinyl alcohols, acetylenic glycols and graphite. Burnout materials may also be used to increase the porosity of the final extrudate. Examples of burnout materials are polyethylene oxide, methyl-cellulose, ethylcellulose, latex, starch, nut shells or flour, polyethylene or any of the polymeric microspheres or microwaxes.

The preparation of a shapable dough from the solids (silica powder and optionally binder), water and extrusion aids can be performed by those methods known in the art for preparing extrudable doughs, such as for instance disclosed in EP-A-309048. Such dough typically has a paste-like appearance. It is within the normal skills of those skilled in the art to optimise the mixing/kneading procedure and to select the appropriate extrusion equipment, to select the appropriate amounts of the ingredients to obtain an extrudable dough, to select the timing of adding the various ingredients and to select the most appropriate extrusion conditions. Typically, the extrudable dough will have a solids content of 23-60% by weight, suitably 27 to 55% by weight. The extrusion aids are typically used in an amount of from 0.5 to 20% by weight, suitably 2 to 15% by weight, on the total solids content of the mixture. The remainder up to 100% by weight is water.

After extrusion the extrudates are calcined in step (b). Calcination is typically effected at a temperature of from 400 to 1000° C., preferably from 450 to 800° C., more preferably from 500 to 700° C. Calcination time may vary within wide limits and may range from 15 minutes to 48 hours. Suitably, the calcination time will be between 1 and 4 hours. The calcination may be preceded by a separate drying step, but this is not required. If applied, such drying step will typically be effected at a temperature up to 300° C., more suitably up to 250° C. The period for drying may vary, but will usually up to 5 hours, more suitably from 30 minutes to 3 hours. The drying may be integrated with the subsequent calcination or, as indicated before, be completely dispensed with.

The calcined extrudate thus obtained may subsequently be treated with water or steam before it is impregnated in step (c). Such hydrolysis treatment may, for instance, involve a pore impregnation treatment with water by soaking or immersing the calcined extrudate in water or steaming the extrudate, e.g. with low pressure steam of 120-180° C. Alternatively, the hydrolysis treatment may comprise a washing treatment using an aqueous solution of a mineral acid, an aqueous solution of an ammonium salt or a combination thereof. Without wishing to be bound by any particular theory it is believed that the hydrolysis treatment is beneficial for re-hyroxylating the silica surface, i.e. restoring any silanol groups on the surface of the silica extrudate which may have been destroyed in the preceding calcination step. Silanol groups, namely, are important for the titanium-containing impregnating agent to react with the silica surface so that it is chemically bonded thereto.

Depending on which hydrolysis treatment is used the conditions at which this treatment is carried out may vary. A water soaking step is normally carried out at ambient temperature, while a steaming step at this stage of the process is suitably carried out at temperatures that typically range from 120 to 180° C.

As indicated, the hydrolysis may also involve a washing treatment using an aqueous solution of a mineral acid, an aqueous solution of an ammonium salt or a combination thereof. Suitable mineral acids in this connection include hydrochloric acid, sulphuric acid, phosphoric acid and the like. Particularly preferred washing liquids are aqueous solutions of hydrochloric acid or sulphuric acid. Other washing liquids which can be used include aqueous solutions of an ammonium salt. Such ammonium salts also include tetramethyl ammonium salts. Examples of suitable ammonium salts, then, include ammonium or tetramethyl ammonium hydroxide, nitrate, acetate, citrate, carbonate, chloride and sulphate. Of these, ammonium acetate is particularly preferred. Concentrations of the mineral acids or ammonium salts in water are not particularly critical and will normally range from 0.01 M to 5 M.

Particularly if the hydrolysis treatment involves washing with a mineral acid solution and/or an ammonium salt solution, an optional additional washing step may be applied: washing with water, preferably with distilled, demineralised or deionised water. If applied, this water wash step may be repeated one or more times. Suitably, the water wash step may be carried out one to six times.

The optional hydrolysis step may be followed by a drying step. Drying may take place in conventional ways known in the art and for the purpose of the present invention it was found particularly suitable to perform the drying in an oxygen-containing atmosphere, suitably air, at a temperature of from 70 to 400° C., more suitably from 110 to 300° C. Alternatively, the drying may take place in an atmosphere other than air, e.g. in a nitrogen atmosphere. Drying time will normally be between 15 minutes and 5 hours.

In step (c) the calcined and optionally hydrolysed (and dried) extrudate is impregnated with a titanium-containing impregnating agent, while in step (d) the impregnated catalyst is dried and calcined. The drying in step (d) may be carried out in the same way as described above in relation to drying of a hydrolysed extrudate. Calcination in step (d) is suitably performed at a temperature of from 400 to 1000° C., preferably 500 to 800° C. Again, calcination time may vary within broad limits and the same ranges apply as indicated hereinbefore in respect of calcination time of the extrudate in step (b).

The impregnating agent used in step (c) may be either a liquid or a vapour. If a liquid impregnating agent is used, an additional drying step may be included between steps (c) and (d) to remove the solvent used in the impregnation solution. Examples of suitable liquid impregnating agents are known in the art and include solutions of titanium tetrahalide, such as titanium tetrachloride or titanium tetrafluoride, in an organic solvent, such as alkanes (e.g. hexane), aromatic compounds (e.g. toluene), alcohols (e.g. methanol, ethanol) or ethers. Other examples include organic titanium complexes such as tetra(isopropyl) titanate, tetra (n-butyl) titanate, tetrakis (trimethylsily) titanate and di(acetoacetyl)di(isopropyl) titanate, the latter being for instance described in JP-A-11/228553. Wet impregnation methods are also well known in the are and in principle any suitable wet impregnation technique may be used. Examples of such techniques are disclosed in GS-1,332, 527;EP-A-734764;WO-98/50374 and U.S. Pat. No. 6,011, 162.

In a preferred embodiment, however, a gaseous titanium-containing impregnating agent is used. A gaseous titanium tetxahalide and in particular gaseous titanium tetrachloride, optionally in conjunction with an inert carrier gas like nitrogen or argon, is very useful in this respect. A method using gaseous titanium tetra-chloride as impregnating agent, followed by calcination, hydrolysis and optionally silyation is described in EF-A-345856. This process is very suitable for the purpose of the present invention.

Accordingly, the present invention also relates to a process for the preparation of a heterogeneous catalyst composition for the epoxidation of olefins into alkylene oxides, which process comprises in addition to steps (a) to (d) mentioned hereinbefore:

(e) hydrolysing the calcined material obtained from step (d), and (f) optionally silylating the product from step (e).

Further details regarding steps (c) through (f) for gas phase impregnation can be found in EP-A-34556, which is incorporated herein by reference. For instance, gas phase impregnation may be carried out using an inert carrier gas at temperatures which suitably are higher than 130° C., more suitably between 150 and 250° C. Hydrolysis step (e) may be carried out by ways known in the art and examples of suitable hydrolysis treatments are described hereinbefore in relation to hydrolyzing the extrudate after step (b) and prior to step (c). However, when steam is applied temperature conditions typically are somewhat more severe than in the optional earlier hydrolysis step between steps (b) and (c). Accordingly, hydrolysis step (e) is suitably effected with steam at a temperature in the range of from 150 to 400° C.

Silylation step (f) can be carried out by ways known in the art, for instance by contacting the product of step (e) with a suitable silylating agent at a temperature between 100 and 300° C. Suitable silylating agents include organosilanes like tetra-substituted silanes with C1-C3 hydrocarbyl substituents. A very suitable silylating agent is hexamethyldisilazane. Examples of suitable silylating methods and silylating agents are, for instance, described in U.S. Pat. Nos. 3,829,392 and 3,923,843 which are referred to in U.S. Pat. No. 6,011,162, and in EP-A-734764.

It is well known in the art to produce alkylene oxides, such as propylene oxide, by epoxidation of the corresponding olefin using an active oxygen species such as hydrogen peroxide or an organic hydroperoxide as the source of oxygen. For instance, a commonly known method for manufacturing propylene oxide is the co-production of propylene oxide and styrene starting from ethylbenzene. In general such process involves the steps of (i) reacting ethylbenzene with oxygen or air to form ethylbenzene hydroperoxide, (ii) reacting the ethyl-benzene hydroperoxide thus obtained with propene in the presence of an epoxidation catalyst to yield propylene oxide and 1-phenyl ethanol, and (iii) dehydrating the 1-phenyl ethanol into styrene using a suitable dehydration catalyst.

Another method for producing propylene oxide is the co-production of propylene oxide and methyl tert-butyl ether (MTBE) starting from isobutane and propene. This process is well known in the art and involves similar reaction steps as the styrene/propylene oxide production process described in the previous paragraph. In the epoxidation step tert-butyl hydroperoxide is reacted with propene forming propylene oxide and tert-butanol. Tert-butanol is subsequently etherified into MTBE.

The heterogeneous catalyst composition of the first aspect of the present invention and as obtainable by the process of the second aspect of the present invention is very suitable as an epoxidation catalyst for promoting the epoxidation of alkenes into the corresponding alkylene oxide. Accordingly, in a third aspect the present invention relates to a process for the preparation of an alkylene oxide by reacting an olefin with an active oxygen species in the presence of the heterogeneous catalyst of the first aspect of the present invention. Suitably, the active oxygen species is an organic hydroperoxide, such as tert-butyl hydroperoxide and ethylbenzene hydroperoxide, the latter being preferred for the purpose of the present invention.

It was surprisingly found that the heterogeneous catalyst of the present invention resulted in an excellent propylene oxide selectivity, i.e. the mole percentage of propene that is converted into propylene oxide, and/or excellent activity when compared to a heterogeneous catalyst based on a silica gel carrier.

The conditions under which the epoxidation reaction is carried out are those conventionally applied in propene epoxidation reactions with ethylbenzene hydroperoxide. Typical reaction conditions include temperatures of 50 to 140° C., suitably 75 to 125° C., and pressures up to 80 bar with the reaction medium being in the liquid phase.

The invention is further illustrated by the following examples without limiting the scope of the invention to these particular embodiments.

In the examples the following ingredients are used:

| | |
|---|---|
| HP321: | particulate silica powder ex Crossfield |
| SIPERNAT 50: | particulate silica powder ex Degussa (SIPERNAT is a trademark) |
| MEOA: | mono-ethanol amine |
| SUPERFLOC N100: | flocculation agent (SUPERFLOC is a trademark) |
| NALCO 7879: | flocculation agent (NALCO is a trademark) |
| PVA: | polyvinylalcohol |

EXAMPLE 1

In this example silica extrudates are prepared and these extrudates are subsequently used to prepare catalyst particles. The ingredients used in their respective amounts were:

| | |
|---|---|
| SIPERNAT 50 (g) | 2867 |
| NALCO 7879 (g) | 100 |
| MEOA (g) | 125 |
| Water (g) | 5550 |
| Additional Water (g) | 250 |

All silica powder was charged into a mixer/muller and the mixing and kneading was started. After 1 minute a solution of MEOA in water was added. After 35, 50 and 60 minutes respectively 125 grams, 50 grams and 75 grams of additional water were added. After 90 minutes the flocculation agent NALCO 7879 was added. After 95 minutes the mixing and kneading stopped. The resulting plastic pieces were subsequently extruded.

Extrusion took place in a 2.25 inch Bonnot extruder provided with a dieplate of a 1.3 mm trilobe. The screw speed in the extruder was 20 rpm (rotations per minute).

The extrudates thus obtained were dried for 2 hours at 120° C. and subsequently the temperature was raised to 800° C. over a period of 3 hours, at which temperature the extrudates were maintained for 2 hours. After cooling the extrudate strings were broken and sieved resulting in trilobes with a diameter of 1.3 mm and a length/diameter ratio of about 3.

The extrudates were subsequently soaked in water for 1 hour, filtered and dried for 2 hours at 120° C. The properties of the extrudates are listed in Table 1.

75 grams of the extrudates were loaded into a quartz reactor tube and heated to 260° C. under a nitrogen flow of 73 Nl/h. The extrudates were kept at 260° C. for 2 hours. Hereafter the extrudates were cooled to 195° C. and 15 grams gaseous titanium tetrachloride ($TiCl_4$) was passed through the bed of extrudates over a period of 70 minutes while a nitrogen flow of 5 Nl/h was maintained as well. After termination of the $TiCl_4$ distillation, dry nitrogen was led over the silica bed for 2 hours at 195° C. and at a rate of 5 Nl/h. The impregnated silica was then heated in a nitrogen atmosphere to 600° C. (at a rate of 50° C./h) and calcined for 6 hours at 600° C. The calcined silica/titania catalyst was cooled to 325° C., while the nitrogen flow was increased to 10 Nl/h. Then steam was added to the nitrogen circulating over the catalyst. Steam treatment was thus carried out by passing steam over the catalyst bed at a rate of 4 g/h for two hours at 325° C. The reactor was subsequently cooled to 200° C. in a stream of dry nitrogen. Hexamethyldisilazane was then passed over the catalyst bed at a rate of 18 g/h for two hours using dry nitrogen as a carrier gas (at a rate of 5 Nl/h). An exotherm of 30° C. was observed, indicating a reaction of hexamethyldisilazane with hydroxyl groups in the catalyst. Excess of hexamethyl-disilazane was stripped with nitrogen (75 Nl/h).

The catalyst particles thus obtained are further referred to as Catalyst 1.

EXAMPLE 2

Example 1 was repeated except that the wet extrudate was passed into a spheroniser after passing through a 0.8 mm cylindrical dieplate. In the spheroniser spheres having a diameter of 1.4 mm were formed. These spheres were subsequently dried, calcined, impregnated with gaseous $TiCl_4$, hydrolysed and silylated as described in Example 1 (Catalyst 2).

EXAMPLE 3

The ingredients used in their respective amounts to prepare the silica extrudates were:

| | |
|---|---|
| HP321 (g) | 169 |
| NALCO 7879 (g) | 5 |
| SUPERFLOC N100 (g) | 4.5 |
| MEOA (g) | 6 |
| PVA, 5% in water (g) | 61 |
| Water (g) | 256 |

All silica powder was charged into a mixer/muller and the mixing and kneading was started. After 3 minutes SUPERFLOC was added and after 13 minutes a solution of MEOA and PVA in water was added. After 40 minutes of mixing and kneading the powdery mix changed into a mix consisting of plastic pieces and to these plastic pieces NALCO was added. After 44 minutes an extrudable mixture was discharged.

Extrusion took place in a 1 inch Bonnot extruder provided with a dieplate of a 0.8 mm trilobe. The screw speed in the extruder was 30 rpm.

The extrudates thus obtained were dried for 2 hours at 120° C. and subsequently the temperature was raised to 550° C. over a period of 2 hours, at which temperature the extrudates were maintained for 2 hours. After cooling the extrudate strings were broken and sieved resulting in trilobes with a diameter of 0.8 mm and a length/diameter ratio of about 3.

The extrudates were subsequently soaked in water for 1 hour, filtered and dried for 16 hours at 120° C. The properties of the extrudates are listed in Table 1.

The extrudates thus obtained were impregnated with gaseous $TiCl_4$, hydrolysed and silylated as described in Example 1 resulting in titania-on-silica catalyst particles (Catalyst 3).

TABLE 1

Extrudate Properties

| | Example 1 | Example 2 | Example 3 |
|---|---|---|---|
| Flat Plate Strength* (N/cm) | 55 | 58 | 71 |
| BET surface** ($m^2/g$) | 245 | 231 | 364 |
| Hg surface area ($m^2/g$) | 263 | 257 | 411 |
| Pore volume*** (ml/g) | 1.27 | 1.21 | 1.06 |

*ASTM D-4179
**BET method ISO 9277: 1995 (E)
***mercury intrusion

EXAMPLE 4

Catalyst 1, Catalyst 2 and Catalyst 3 were used as catalyst in epoxidation experiments to convert ethyl-benzene hydroperoxide with propene into propylene oxide and 1-phenyl ethanol.

The epoxidation experiments were carried out in a continuous epoxidation bench scale unit containing two vessels on automatic weight balances containing respectively the EBHP and alkene feed streams, two high pressure pumps, a fixed bed reactor, a third pump for pumping a recycle stream over the reactor, means to maintain the reactor continuously at temperatures between 60 and 120° C., a stripper to remove light boiling components like propene, a cooler and a vessel for receiving the product.

The feeds were supplied to the reactor via the two high pressure pumps and mixed together before entering the reactor. The reactor was operated liquid full at 40 bara pressure. A large recycle stream was maintained over the reactor to have isothermal operation of the reactor bed and to ensure that the catalyst to be re-activated is contacted with epoxidation reaction product. The feed of propene and a 35 wt % EBHP solution in ethylbenzene was mixed with the recycle stream prior to introduction into the reactor.

A compositional analysis of the reaction mixture was carried out by means of Super Critical Fluid Chromatography (SFC).

The following process conditions were maintained:

| | |
|---|---|
| throughput EBHP solution: | 30 grams/hour |
| throughput propene: | 18 grams/hour |
| recycle flow: | 2.5 kg/hour. |

The activity of the catalyst is expressed as "K85" indicating the reaction rate constant in $kg^2$ of liquid per kg of catalyst per mole per hour ($kg^2/(kg*mole*h)$) normalised at 85° C. assuming that first order reaction kinetics apply in EBHP and in propene. The K85 is determined as the mean K85 over 300 hours of operation at 90° C.

The selectivity of the catalyst is calculated as the mean selectivity to propene over a period of 300 hours at 90° C.

The results are indicated in Table 2.

TABLE 2

Epoxidation results

| | Catalyst 1 | Catalyst 2 | Catalyst 3 |
|---|---|---|---|
| K85 (kg$^2$/(kg*mole*h)) | 18.8 | 20.0 | 34.9 |
| Selectivity (wt %) | 95.0 | 95.2 | 95.3 |

COMPARATIVE EXAMPLE 1

Example 1 was repeated except that the extrusion part was not carried out. Instead, 75 grams of a commercial silicagel (G57 ex Grace) was loaded into the quartz reactor tube. The resulting catalyst was used as an epoxidation catalyst according to the procedure described in example 4, giving a K85 of 14.0 kg$^2$/kg*mole*h and a selectivity of 90.4 wt %.

We claim:

1. A process for the preparation of a heterogeneous catalyst suitable for the epoxidation of olefins into alkylene oxides, which process comprises the steps of:
    (a) extruding silica powder into an extrudate having a selected shape;
    (b) calcining the extrudate;
    (c) impregnating the calcined extrudate with a gaseous titanium-containing impregnating agent; and
    (d) drying and calcining the impregnated extrudate.

2. The process as defined in claim 1, wherein after step (b) and prior to step (c) the calcined extrudate is hydrolyzed.

3. The process as defined in claim 1, which process comprises the additional steps of:
    (e) hydrolyzing the calcined material obtained from step (d); and
    (f) optionally silylating the product from step (e).

4. A process for the preparation of an alkylene oxide by reacting an olefin with an active oxygen species in the presence of a heterogeneous catalyst prepared by the process of claim 1.

5. The process as defined in claim 4, wherein the active oxygen species is an organic hydroperoxide.

6. The process as defined in claim 1, wherein the silica powder is a precipitated silica powder or a silica gel ground into a powder.

7. The process as defined in claim 1, wherein the calcined shaped extrudate has a surface area in the range of from 100 m$^2$/g to 1000 m$^2$/g, a pore volume in the range of from 0.5 ml/g to 2.5 ml/g and an average pore diameter as determined by mercury intrusion in the range of from 3 nm to 40 nm.

8. The process as defined in claim 1, wherein the shape of the calcined shaped extrudate is selected from the group consisting of a sphere, a trilobe, a quadrulobe, a ring, a massive cylinder and a hollow cylinder and the average particle size of the calcined shaped extrudate ranges from 0.5 to 10 mm.

9. The process as defined in claim 2, which process comprises the additional steps of:
    (e) hydrolyzing the calcined material obtained from step (d); and
    (f) optionally silylating the product from step (e).

10. A process for the preparation of a heterogeneous catalyst suitable for the epoxidation of olefins into alkylene oxides, which process comprises the steps of:
    (a) extruding dough comprising silica powder into an extrudate having a selected shape;
    (b) calcining the extrudate to produce calcined shaped extrudate comprising silica powder;
    (c) exposing said calcined shaped extrudate comprising silica powder to impregnating agent comprising titanium under impregnation conditions effective to produce impregnated calcined shaped extrudate comprising said impregnated agent; and
    (d) drying and calcining the impregnated calcined shaped extrudate comprising silica powder under calcining conditions effective to produce calcined shaped extrudate comprising titanium consisting essentially of titanium chemically bonded to a surface of said calcined shaped extrudate.

11. The process as defined in claim 10, which process comprises the additional steps of:
    (e) hydrolyzing the impregnated calcined shaped extrudate; and
    (f) optionally silylating the product from step (e).

12. A process for the preparation of an alkylene oxide by reacting an olefin with an active oxygen species in the presence of a heterogeneous catalyst prepared by the process of claim 10.

13. The process as defined in claim 12, wherein the active oxygen species is an organic hydroperoxide.

14. A process as defined in claim 10, wherein said silica powder is selected from the group consisting of precipitated silica powder and silica gel ground into powder.

15. The process as defined in claim 10, wherein the calcined shaped extrudate has a surface area in the range of from 100 m$^2$/g to 1000 m$^2$/g, a pore volume in the range of from 0.5 ml/g to 2.5 ml/g and an average pore diameter as determined by mercury intrusion in the range of from 3 nm to 40 nm.

16. A process as defined in claim 10, wherein the shape of the calcined shaped extrudate is selected from the group consisting of a sphere, a trilobe, a quadrulobe, a ring, a massive cylinder and a hollow cylinder and the average particle size of the calcined shaped extrudate ranges from 0.5 to 10 mm.

* * * * *